(12) United States Patent
Brodsky et al.

(10) Patent No.: US 8,740,902 B2
(45) Date of Patent: Jun. 3, 2014

(54) JOINT FUSION APPARATUS FOR THE ANKLE-TYPE JOINT AND ARTHRODETIC PIN FOR USE IN SAID APPARATUS

(75) Inventors: James White Brodsky, Dallas, TX (US); Bertrand Xavier François Gauneau, Lyons (FR)

(73) Assignee: Newdeal, Saint Priest (FR)

( * ) Notice: Subject to any disclaimer, the term of this patent is extended or adjusted under 35 U.S.C. 154(b) by 1178 days.

(21) Appl. No.: 11/914,286

(22) PCT Filed: May 12, 2006

(86) PCT No.: PCT/FR2006/001070
§ 371 (c)(1),
(2), (4) Date: Nov. 19, 2008

(87) PCT Pub. No.: WO2006/120355
PCT Pub. Date: Nov. 16, 2006

(65) Prior Publication Data
US 2009/0149861 A1    Jun. 11, 2009

(30) Foreign Application Priority Data
May 13, 2005  (FR) ..................................... 05 04851

(51) Int. Cl.
*A61B 17/56* (2006.01)
*A61B 17/58* (2006.01)
*A61F 2/30* (2006.01)

(52) U.S. Cl.
USPC ......................................................... 606/62

(58) Field of Classification Search
USPC ................. 606/55, 57–59, 96–100, 104, 105;
623/20.32, 21.18, 21.19, 21.11–21.13
See application file for complete search history.

(56) References Cited

U.S. PATENT DOCUMENTS 4,875,475 A * 10/1989 Comte et al. ..................... 606/64
4,913,137 A * 4/1990 Azer et al. ....................... 606/64
(Continued)

FOREIGN PATENT DOCUMENTS

| EP | 1393696 A1 | 3/2004 |
| WO | 2004014243 A1 | 2/2004 |

OTHER PUBLICATIONS

DePuyACE (a Johnson-Johnson company), "Surgical Techniqe: Tibotalocalcaneal Fusion Using the VersaNail", available on website: http://www.rcsed.ac.uk/fellows/lvanrensburg/classification/surgtech/depuy/depuy%20manuals.htm in 2004.*

(Continued)

*Primary Examiner* — Mary Hoffman
*Assistant Examiner* — Michelle C Eckman
(74) *Attorney, Agent, or Firm* — Jason A. Bernstein; Barnes & Thornburg LLP (57) ABSTRACT

Arthrodesis apparatus for first and second bones (2, 3), comprising a nail (5) and an instrument (20) for putting the nail (5) into place, the instrument comprising a base (21) and compression means (22, 23) comprising control means (22) for causing the nail to move relative to the base (21) and holder means (23) for holding the second bone (3) relative to the base (21); a guide (11) for the nail, the guide (11) and the holder (23) being arranged and shaped to cooperate together in such a manner to as allow the nail to move relative to the holder (23) and move the first bone (2) and the second bone (3) towards each other.

27 Claims, 4 Drawing Sheets

(56) References Cited

U.S. PATENT DOCUMENTS

| | | | |
|---|---|---|---|
| 5,108,398 A * | 4/1992 | McQueen et al. | 606/62 |
| 5,281,224 A * | 1/1994 | Faccioli et al. | 606/62 |
| 5,352,228 A * | 10/1994 | Kummer et al. | 606/64 |
| 5,643,258 A * | 7/1997 | Robioneck et al. | 606/54 |
| 5,665,086 A * | 9/1997 | Itoman et al. | 606/64 |
| 5,766,174 A * | 6/1998 | Perry | 606/62 |
| 5,766,179 A * | 6/1998 | Faccioli et al. | 606/98 |
| 6,197,029 B1 * | 3/2001 | Fujimori et al. | 606/62 |
| 6,579,293 B1 * | 6/2003 | Chandran | 606/64 |
| 2002/0151898 A1 | 10/2002 | Sohngen et al. | |
| 2003/0097131 A1 * | 5/2003 | Schon et al. | 606/62 |
| 2004/0215204 A1 * | 10/2004 | Davison et al. | 606/98 |
| 2005/0010223 A1 * | 1/2005 | Gotfried | 606/62 |
| 2005/0107791 A1 * | 5/2005 | Manderson | 606/62 |
| 2006/0173457 A1 * | 8/2006 | Tornier | 606/62 |
| 2006/0200141 A1 * | 9/2006 | Janna et al. | 606/62 |
| 2009/0048598 A1 * | 2/2009 | Ritchey et al. | 606/57 |

OTHER PUBLICATIONS

Screen capture of website: http://www.rcsed.ac.uk/fellows/lvanrensburg/classification/surgtech/depuy/depuy%20manuals.htm Aug. 16, 2004 using the Wayback Machine found at www.archive.org.*

Search Report for International Patent Application No. PCT/FR2006/001070; Sep. 14, 2006.

* cited by examiner

JOINT FUSION APPARATUS FOR THE ANKLE-TYPE JOINT AND ARTHRODETIC PIN FOR USE IN SAID APPARATUS

PRIORITY CLAIM

This patent application is a U.S. National Phase of International Application No. PCT/FR2006/001070, filed May 12, 2006, which claims priority to French Patent Application No. 0504851, filed May 13, 2005, the disclosures of which are incorporated herein by reference in their entirety.

FIELD

The present disclosure relates to apparatus designed for use in performing an arthrodesis. The present disclosure also relates to an arthrodesis apparatus for a joint formed at least by a first bone and by a second bone, such as the ankle joint.

The present disclosure also relates to an arthrodesis nail for use within an arthrodesis apparatus.

The present disclosure also relates to a surgical method of performing arthrodesis of the ankle using an arthrodesis apparatus.

In a preferred but non-exclusive application, the apparatus in accordance with the present disclosure is intended and is designed for performing arthrodesis of the ankle joint, it being understood that applications to other joints, and in particular to the shoulder joint, could also be envisaged.

BACKGROUND

Arthrodesis is surgery for the purpose of almost completely eliminating the mobility of a joint by giving rise to "bone fusion". Such surgery can be necessary when the patient is suffering from severe and final arthrosis.

To perform such surgery, it is known to make use of arthrodesis apparatus comprising firstly an arthrodesis nail that is to be implanted within the joint, and secondly an instrument for putting the arthrodesis nail into place.

The arthrodesis nail is generally inserted into housings formed in succession through the various bones making up the joint, and the arthrodesis nail includes fastener holes that are designed to cooperate with fastener screws in order to secure the arthrodesis nail with the bones forming the joint.

In order to put such arthrodesis nails into place, it is known to use an instrument including compression means to move together the bones forming the joint and, for example, with an ankle joint, serving to bring the calcaneus closer to the tibia.

The compression step is very important in the surgery, insofar as this step determines the relative positioning of the bones constituting the joint, and poor positioning can constitute a difficulty for the patient.

Unfortunately, with the ankle joint the compression means are generally implemented with the help of a bearing surface arranged to bear against the heel and suitable for being moved in order to exert pressure thereagainst so as to move the calcaneus and the tibia closer together.

The operating technique generally used is as follows:
the surgeon uses a fastener screw to secure the arthrodesis nail to the tibia;
thereafter, the surgeon moves the bearing surface so that it comes to bear against the heel and compresses the joint, thereby moving the tibia and the calcaneus closer together; and
finally, the surgeon secures the nail to the calcaneus while maintaining the pressure exerted by the bearing surface against the heel.

Although arthrodesis apparatus in the prior art are advantageous in terms of preventing the joint from moving, the arthrodesis apparatus, nevertheless, suffers from drawbacks that are not negligible.

In particular, with prior art apparatus, there is a risk during the compression step of the nail going through the cortex of the calcaneus adjacent to the sole and projecting from the sole face.

With such an apparatus, the surgeon must take particular care not to apply excessive compression to the joint. Such a constraint constitutes a non-negligible drawback for the surgeon, particularly since it is often difficult or even impossible with prior art apparatus to monitor accurately the magnitude of the compression.

Furthermore, the use of apparatus of the prior art can lead to damage to the soft tissue of the face of the sole, tissue situated between the compression bearing surface and the calcaneus.

If the intensity of compression is too great, then the pressure exerted by the bearing surface can lead to necrosis of the skin on the heel.

Furthermore, fastener screws are mounted in the calcaneus and the talus after the compression step, i.e., after the talus and the calcaneus have moved relative to the tibia, so the fastener screws are poorly positioned in the bone, i.e., they can be positioned too close to the periphery of the bone or even positioned in the junction zone between two bones. An arthrodesis nail fastened in that way can then no longer hold the joint correctly.

SUMMARY

The present disclosure describes several exemplary embodiments of the present invention.

One aspect of the present disclosure provides an arthrodesis apparatus for a joint formed by at least a first bone and a second bone, such as the ankle joint, the apparatus, comprising a) an arthrodesis nail having a fastener to fasten the nail to the bones constituting the joint; b) an instrument for putting the arthrodesis nail into place within the joint, the instrument comprising a base and compression means designed to enable the first and second bones forming the joint to be moved towards each other; and c) link means serving as an interface between the instrument and the arthrodesis nail; wherein the compression means comprise control means arranged in such a manner as to act via the link means to move the arthrodesis nail relative to the base along a longitudinal axis substantially parallel to the axis along which the nail extends and holder means arranged to prevent the second bone from moving relative to the base; wherein the nail comprises guide means, the guide means and the holder means being arranged and shaped to cooperate together in such a manner to as allow the nail to move relative to the holder means and to enable the first bone and the second bone to be moved towards each other once the nail has been secured to the first bone.

Another aspect of the present disclosure provides an arthrodesis nail for a joint formed at least by a first bone and by a second bone, the nail having fastener means and guide means, and being designed to be used in an arthrodesis apparatus provided with holder means arranged to prevent the second bone from moving relative to the base, the guide means and the holder means being arranged and shaped to cooperate together in such a manner as to allow the nail to move relative to the holder means, and to enable the first bone and the second bone to be moved towards each other once the nail has been secured to the first bone.

A further aspect of the present disclosure provides a method for performing arthrodesis of the ankle joint incorporating an arthrodesis apparatus comprising an arthrodesis nail and an instrument provided with compression means, the method, comprising a) securing the nail to the calcaneus; and b) compressing by moving the calcaneus closer to the tibia by moving the nail relative to the tibia with the help of the compression means, and controlling the amplitude of the displacement of the nail with the help of guide means provided on the nail.

Consequently, the features of the present disclosure provide a remedy to the various drawbacks mentioned above and provide an arthrodesis apparatus for a joint of the ankle-joint kind, that makes it possible to perform effective compression of the joint without running the risk of damaging either the cortex or the soft tissue close to the bones forming the joint.

Another feature of the present disclosure provides an arthrodesis apparatus presenting good overall stiffness during the compression step.

Another feature of the present disclosure provides an arthrodesis apparatus enabling compression of the joint to be performed in controlled and accurate manner.

Another feature of the present disclosure provides an arthrodesis apparatus enabling the arthrodesis nail to be fastened in a manner that is adapted to the anatomy of the joint.

Another feature of the present disclosure provides an arthrodesis apparatus that ensures the joint is held comfortably.

Another feature of the present disclosure provides as arthrodesis apparatus facilitating mounting of the nail fastener screws relative to the bones forming the joint.

Another feature of the present disclosure provides an arthrodesis apparatus that can be modulated as a function of the anatomy of the joint while also being simple to use.

Another feature of the present disclosure provides an arthrodesis apparatus that is easier to handle and that reduces operator error.

The features of the present disclosure provide an arthrodesis nail that is designed to be used within the arthrodesis apparatus.

The features of the present disclosure provide a surgical method for performing arthrodesis of the ankle in which effective and controlled compression of the joint is achieved without damaging either the bones forming the joint or the adjacent soft tissue.

The present disclosure also describes an arthrodesis apparatus for a joint formed at least by a first bone and by a second bone, such as the ankle joint, the apparatus comprising an arthrodesis nail provided with fastener means for fastening to the bones constituting the joint; an instrument for putting the arthrodesis nail into place within the joint, the instrument comprising a base and compression means designed to enable the first and second bones forming the joint to be moved towards each other; and link means serving as an interface between the instrument and the arthrodesis nail; the apparatus comprising control means arranged in such a manner as to act via the link means to move the arthrodesis nail relative to the base along a longitudinal axis substantially parallel to the axis along which the nail extends; and holder means arranged to prevent the second bone from moving relative to the base; the nail including guide means, the guide means and the holder means being arranged and shaped to cooperate together in such a manner to as allow the nail to move relative to the holder means and to enable the first bone and the second bone to be moved towards each other once the nail has been secured to the first bone.

The present disclosure also provides an arthrodesis nail used in the above-mentioned arthrodesis apparatus.

The present disclosure also provides a surgical method of performing arthrodesis of the ankle joint, in which an arthrodesis apparatus is used that comprises an arthrodesis nail and compression means, the surgical method comprising securing the nail to the calcaneus; and compressing by moving the calcaneus closer to the tibia by moving the nail relative to the tibia with the help of the compression means, and controlling the amplitude of the displacement of the nail with the help of guide means formed on the nail.

BRIEF DESCRIPTION OF THE DRAWINGS

Other advantages and features of the present disclosure appear in greater detail on reading the following description and with the help of the accompanying drawings that are provided purely by way of non-limiting illustration.

DETAILED DESCRIPTION

FIGS. 1, 3, 4, and 5 show an exemplary arthrodesis apparatus 1 in accordance with the present disclosure. Such an apparatus is designed to be used when performing arthrodesis, in particular when a joint, and more particularly an ankle joint, is in such a degraded state that other, less-severe surgical operations, such as those that include implanting an ankle prosthesis, for example, would be ineffective. Under such circumstances, it becomes necessary to prevent the joint completely from moving.

For purposes of the present disclosure, the joint is made up of at least two bones, namely a first bone 2 and a second bone 3, but the joint may also include a third bone 4 situated between the first and second bones 2 and 3.

The arthrodesis apparatus 1 of the present disclosure is particularly adapted to repairing the ankle joint. Nevertheless, the arthrodesis apparatus 1 can also be used for other arthrodesis operations, such as centro-medullary nailing, without going beyond the scope of the present disclosure. For these other applications, it is nevertheless necessary to provide adaptations, in particular, in terms of dimensions.

In the description below, reference is made to the first bone 2, to the second bone 3, and optionally to the third bone 4 forming the joint, it being understood that if the joint is an ankle joint, then the first bone 2 corresponds to the calcaneus, the second bone 3 corresponds to the tibia, and the third bone 4 corresponds to the talus.

Figure 1:
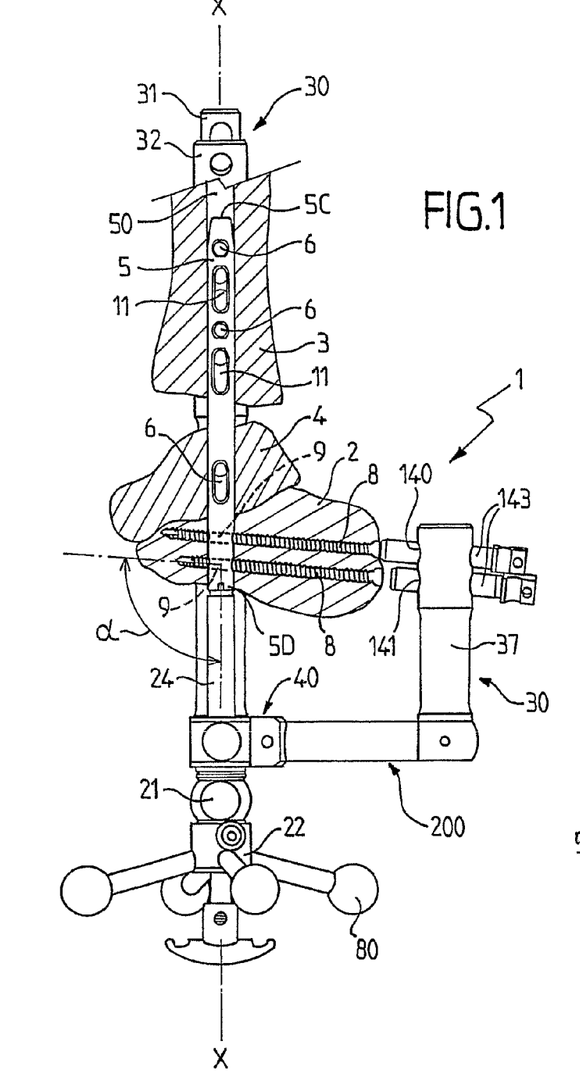
FIG. 1 is a side view showing a portion of an arthrodesis apparatus during the step of securing the arthrodesis nail with the calcaneus.
Figure 5:
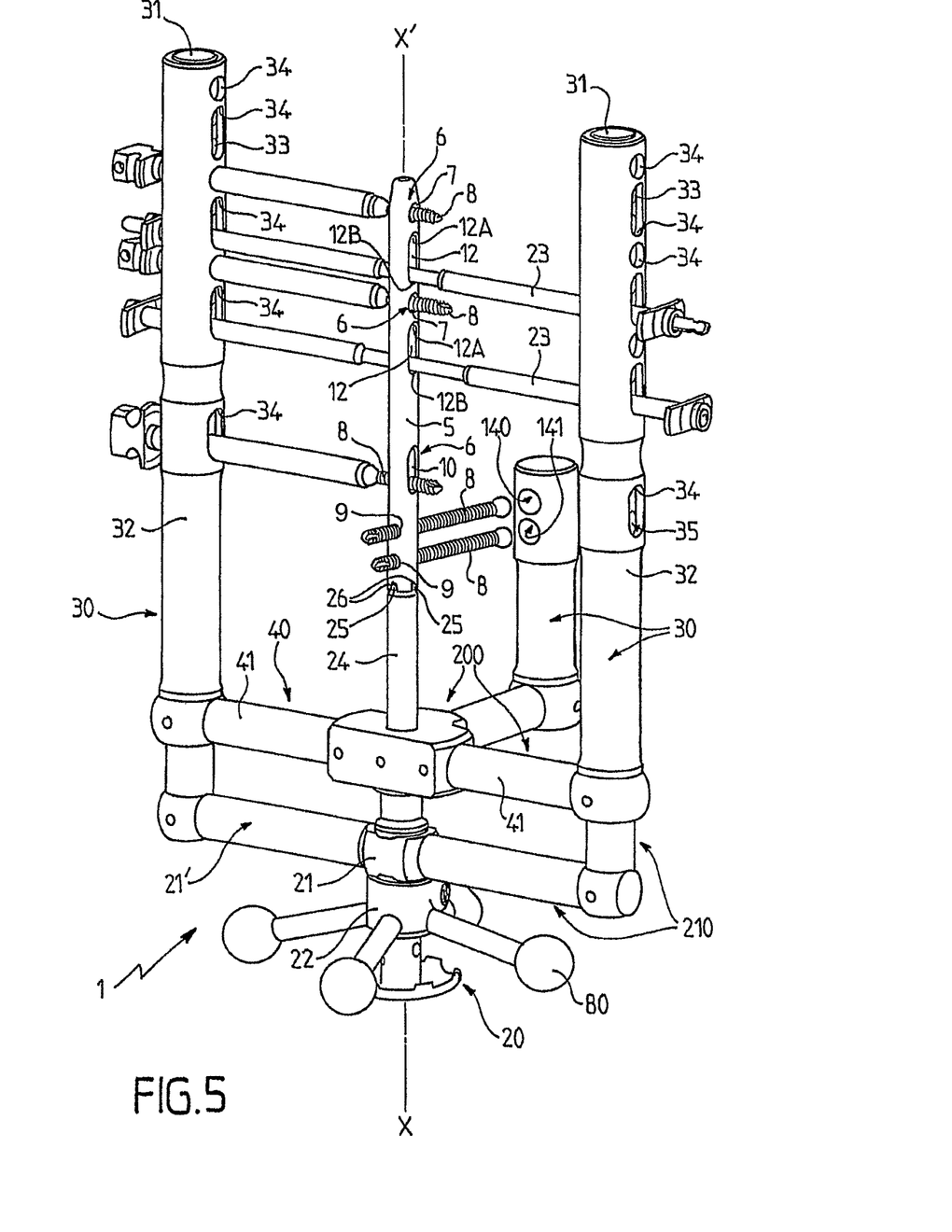
FIG. 5 is a perspective view showing an arthrodesis apparatus while fastening the arthrodesis nail (joint not shown)

According to the present disclosure, the arthrodesis apparatus 1 includes an arthrodesis nail 5 provided with fastener means 6 for fastening to the bones 2, 3, 4 constituting the joint (FIGS. 1 and 5).

Figure 2:
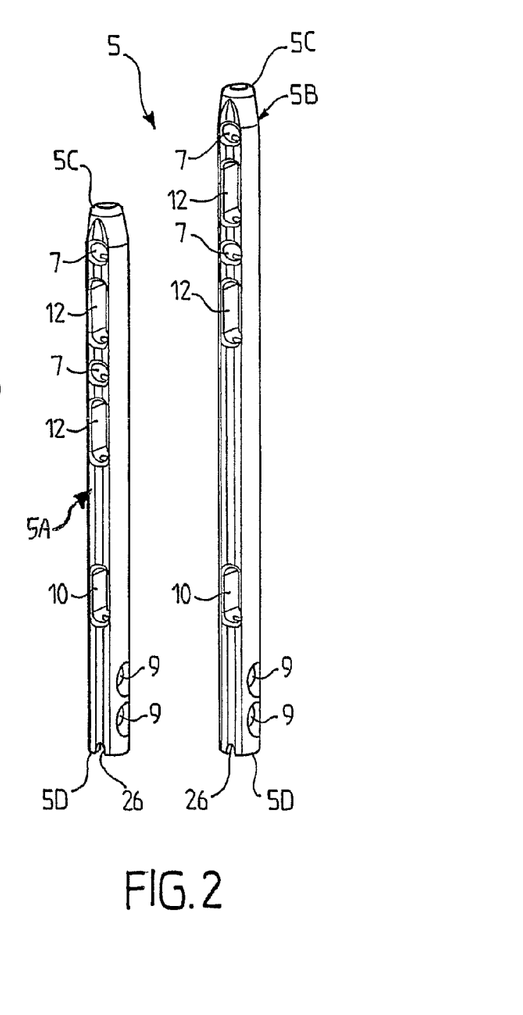
FIG. 2 is a perspective view showing two variant exemplary embodiments of arthrodesis nails.
Figure 3:
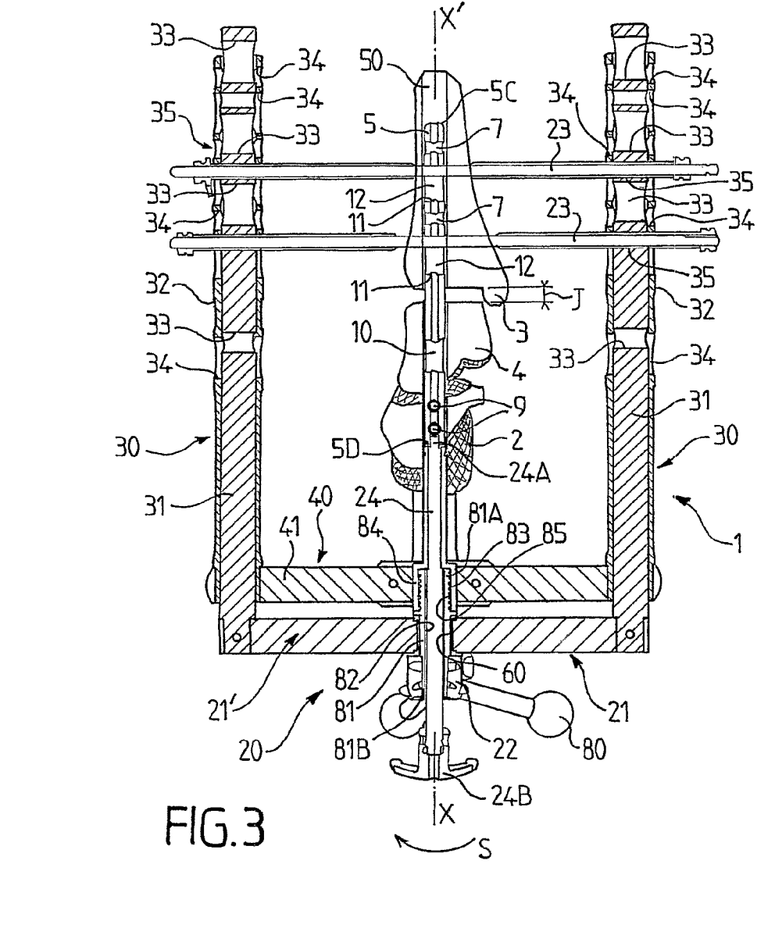
FIG. 3 is a face view showing an arthrodesis apparatus in its position prior to applying compression.

As shown in FIGS. 1-3, the nail 5 is advantageously in the form of a preferably-hollow cylinder that extends between two ends 5C, 5D. One of the ends 5C is preferably slightly chamfered so as to make it easier to implant within the joint. The nail 5 is advantageously made of a metal material that is naturally biocompatible or that is made biocompatible by appropriate treatment.

In a preferred exemplary embodiment, the nail 5 is a single piece.

In particularly advantageous manner, the arthrodesis nail 5 is mounted inside a housing formed within the joint, with the housing having at least one portion in each of the bones 2, 3, 4 constituting the joint, such that the nail 5 extends along a longitudinal axis X-X' parallel to the extension axis of the second bone 3, e.g., the tibia.

Figure 4:
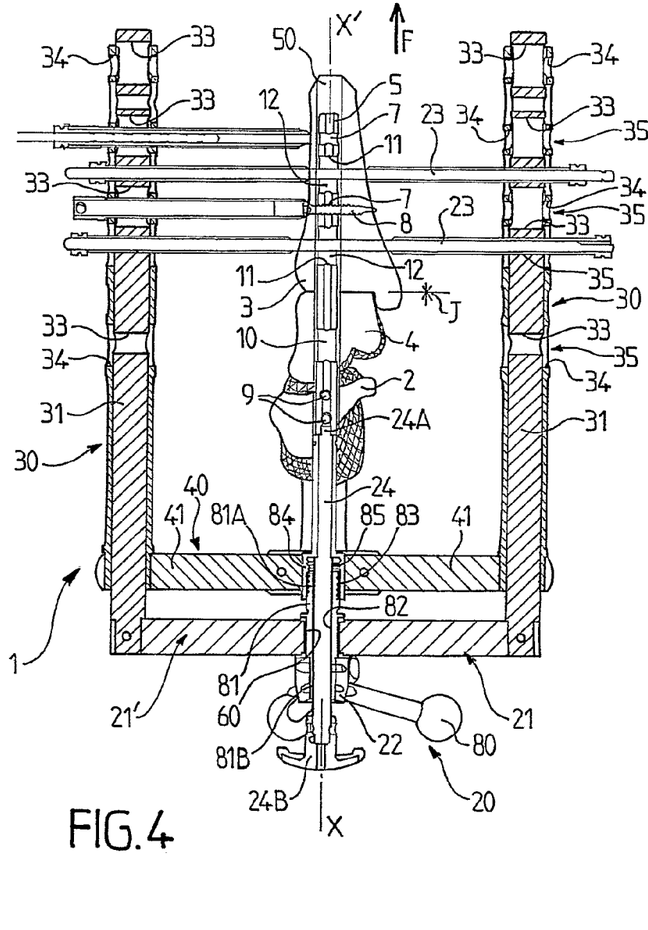
FIG. 4 is a face view of an arthrodesis apparatus in its position after compression has been applied.

Advantageously, the fastener means 6 include two fastener holes 7 (FIGS. 3-5). Each of the fastener holes 7 is advantageously designed to co-operate with at least one fastener screw 8 that is associated therewith in such a manner as to secure the nail 5 to the second bone 3 (FIG. 4). Naturally, the fastener means 6 could include a single hole 7, but the configuration with two fasteners holes 7 is preferred since, a priori, that guarantees better retention of the nail within the joint.

The fastener means 6 for the nail 5 preferably include at least one fastener orifice 9 for cooperating with at least one associated fastener screw 8 so as to secure the nail 5 to the first bone 2 (FIGS. 1, 3, and 4). The fastener screws 8 used are those that are conventionally used in this field and they are well known to the person skilled in the art.

Preferably, the fastener orifice 9 extends obliquely relative to the longitudinal axis X-X', i.e., the fastener orifice 9 forms a duct, preferably a substantially cylindrical duct, extending along a main axis that is oblique relative to the longitudinal axis X-X'. This obliqueness is intended, in particular, to improve the fastening of the nail in the first bone 2, e.g., the calcaneus, taking account of the particular anatomy thereof.

In particularly advantageous manner, the oblique fastener orifice 9 extends along an extension direction Y-Y' forming an angle $\alpha$ lying in the range 95° to 100° relative to the longitudinal axis X-X' (FIG. 1).

In an even more advantageous manner, and as shown in FIG. 1, the fastener means 6 include two fastener orifices 9 for the first bone 2. These two fastener orifices 9 preferably extend obliquely relative to the longitudinal axis X-X'.

Advantageously, and as shown in FIGS. 3-5, the fastener means 6 include a fastener opening 10 arranged to receive an associated fastener screw when the joint includes a third bone 4, e.g., the talus, situated between the first bone 2 and the second bone 3, so as to secure the nail 5 substantially with the third bone 4.

Naturally, when the joint does not have a third bone 4, or when the joint does include a third bone 4 but the third bone 4 is highly degraded, such a fastener opening 10 is not necessary.

In a particularly advantageous manner, the fastener opening 10 is preferably oblong, i.e., the fastener opening 10 is preferably elongate in the direction parallel to the longitudinal axis X-X'. A fastener opening 10 having such a shape is preferred to an opening having a circular shape so as to permit a certain amount of axial mobility to the third bone 4 along the direction of the longitudinal axis X-X', in order to significantly improve patient comfort.

According to the present disclosure, the arthrodesis apparatus 1 comprises an instrument 20 for putting the arthrodesis nail 5 into place within the joint.

The instrument 20 has a base 21 that is stationary during the surgery and compression means 22, 23 for enabling the first and second bones 2 and 3 forming the joint to be moved towards each other.

According to the present disclosure, the arthrodesis apparatus 1 also comprises link means 24 serving as an interface between the instrument 20 and the arthrodesis nail 5.

The link means 24 may advantageously be in the form of a rod, suitable for moving longitudinally along the longitudinal axis X-X'. In particular, the link means 24 and the base 21 are preferably arranged in such a manner that the link means 24 can slide inside the base 21 (FIGS. 3-4).

For this purpose, the base 21 is preferably formed by a compression structure 210 that is preferably stationary and made of metal, within which there is formed a bore 60 enabling the rod 24 to pass (FIGS. 3-4).

The arthrodesis nail 5 preferably rests on the link means 24 in such a manner that moving the link means 24 entrains substantially identical movement in the nail 5.

The link means 24 advantageously extend between two ends 24A and 24B (FIGS. 3-4), and the end 24A is preferably in the form of a threaded endpiece, onto which the corresponding end 5D of the nail 5 is designed to be engaged and screw-fastened.

In order to facilitate positioning the nail 5 relative to the link means 24 and to ensure that the surgeon is not mistaken about the orientation of the nail 5, the link means 24 and the nail 5 advantageously include marker means 25, 26.

As shown in FIG. 5, the marker means 25, 26 are preferably in the form of three studs 25 and three slots 26 arranged in such a manner that each slot 26 can be associated with only one corresponding stud 25.

As shown in FIG. 2, the slots 26 are preferably formed in the end 5D of the nail 5 that is to come into contact with the corresponding end 24A of the link means 24 on which the studs 25 are provided.

Naturally, it is also possible to envisage providing the nail 5 with studs that are for cooperating with corresponding slots provided in the link means 24.

In a preferred exemplary embodiment of the present disclosure, the marker means 25, 26 comprise three pairs, each pair being formed by one stud 25 and one slot 26, the pairs are situated around the junction between the nail 5 and the link means 24, and are oriented substantially at 90° relative to one another.

Such a configuration for the marker means 25, 26 makes it possible, in particular, to avoid the surgeon mounting the nail in an orientation other than the intended orientation, which would lead to the fastener means 6 of the nail 5 being wrongly oriented relative to the bones 2, 3, and 4 constituting the joint.

As shown in FIG. 5, the nail 5 is advantageously engaged on the link means 24 via one of its ends 5D so as to occupy a stable and unchanging insertion position.

According to the present disclosure, the compression means 22, 23 comprise control means 22 arranged in such a manner as to cause the arthrodesis nail 5 to move relative to the base 21 by acting via the link means 24.

Preferably, the control means 22 are in the form of a handwheel 80 (or a knob) mounted on the base 21 (or on the compression structure 210) to turn about the longitudinal axis X-X' by means of a hollow rod 81 (FIGS. 3-4).

The hollow rod 81 is mounted so as to be capable of turning about the longitudinal axis X-X' within the bore 60.

The hollow rod 81 has an internal passage 82 within which the link means 24 can slide along the longitudinal axis X-X'.

The hollow rod 81 extends between a first end 81A provided with an outside thread 83, and a second end 81B secured to the handwheel 80, such that turning the handwheel 80 about the longitudinal axis X-X' leads to the hollow rod 81 turning identically.

As shown in FIGS. 3-4, the link means 24 are fastened to a hollow endpiece 84 having an inside thread 85 suitable for cooperating with the outside thread 83 of the hollow rod 81, such that turning the handwheel 80 in the direction of rotation S causes the hollow rod 81 to turn, and by cooperation between the inside and outside threads 85, 83, causes the hollow endpiece 84 and the associated link means 24 and nail 5 to be moved in translation along a compression direction F (FIG. 4) parallel to the longitudinal axis X-X'.

Thus, turning the control means 22 relative to the base 21 causes the associated link means 24 and the nail 5 to move in translation along the longitudinal axis X-X'.

Without going beyond the scope of the present disclosure, it is possible to envisage replacing the handwheel 80 by any other suitable control means, e.g., a compression pistol-grip of the ratchet type (not shown), which has the advantage, in particular, of providing good control over the magnitude of the compression force applied.

According to the present disclosure, the compression means 22, 23 also comprise holder means 23 arranged to prevent the second bone 3, e.g., the tibia, from moving relative to the base 21, and more precisely relative to the compression structure 210 (FIG. 1).

It is preferable to prevent the second bone 3 from moving in order to avoid movement of the nail 5 leading to movement of the second bone 3.

Naturally, the nail 5 can move relative to the second bone 3 only if the second bone has not yet been secured to the nail 5 by means of the fastener screws 8, which means that it is necessary to perform the compression step during which the arthrodesis nail 5 is caused to move within the joint, before performing the step of fastening the nail 5 relative to the second bone 3.

According to the present disclosure, the nail 5 includes guide means 11, the guide means 11 and the holder means 23 are arranged and shaped so as to cooperate with each other in such a manner as to allow the nail 5 to move relative to the holder means 23 and, once the nail 5 is secured to the first bone 2, to enable the first and second bones 2 and 3 to be moved towards each other.

Thus, in order to enable the first bone 2 to move closer to the second bone 3, it is preferable to begin by securing the nail 5 to the first bone 2 with the help of the fastener means 6, e.g., by causing the fastener orifices 9 to cooperate with fastener screws 8 (FIG. 1).

Thus, when the nail 5 is secured to the first bone 2, actuating the control means 22 enables the nail 5 and the associated first bone 2 to be moved so as to bring the first bone 2 and the second bone 3 closer together.

By means of this configuration and, in particular, by means of the cooperation between the guide means 11 and the holder means 23, it is possible to compress the joint in an effective manner while making use of the particular arrangement of the guide means 11 to control the amplitude of the displacement of the nail 5 and thus the intensity of the compression.

In addition, since the first bone 2 is secured to and moves with the nail 5 during compression, use of the apparatus 1 reduces, or even completely eliminates, any risk of perforating the cortex of the first bone 2 with the nail 5 during compression.

Thus, as shown in FIGS. 3-4, the guide means 11 are formed by at least one oblong cavity 12 that presents a shape that is substantially elongate along the longitudinal axis X-X'. The oblong cavity 12 is preferably formed in the thickness of the nail 5 so as to extend along an axis that intersects the longitudinal axis X-X'. Thus, the oblong cavity 12 may extend, for example, in depth along an axis that is perpendicular to the longitudinal axis X-X'.

In a preferred exemplary embodiment of the present disclosure, the oblong cavity 12 is a through cavity, i.e., the oblong cavity 12 opens out on both sides of the arthrodesis nail 5.

The oblong cavity 12 preferably extends over a length of about 12 millimeters (mm) along the longitudinal axis X-X' so as to permit a substantially equivalent movement of the nail 5 during compression. The ends 12A, 12B of the cavity 12 that are in alignment on the longitudinal axis X-X' advantageously form abutment means acting against the holder means 23 (FIG. 5).

In more preferred manner, the guide means 11 are formed by at least two cavities 12 formed one above the other along the nail 5 and in alignment with each other along the longitudinal axis X-X' (FIGS. 3-4).

Advantageously, the fastener holes 7, the cavities 12, and the fastener opening 10 all pass through the nail 5 along axes that are substantially perpendicular to the axes along which the fastener orifices 9 extend so as to enable the second and third bones 3 and 4 to be fastened by a lateral approach, while on the contrary enabling the first bone 2 to be fastened by an anterior-posterior approach.

Advantageously, the means for holding the second bone 3 are formed by at least one holder rod 23 shaped in such a manner as to pass at least in part both through the oblong cavities 12, and through the second bone 3 in order to hold the second bone stationary relative to the base 21 (FIGS. 3-4).

By means of the particular arrangement of the holder rod 23 and of the oblong cavity 12, the nail 5 can move relative to the holder rod 23 over a maximum length that corresponds substantially to the length of the oblong cavity 12, i.e., preferably a length of about 12 mm.

In a still more advantageous manner, the holder means are formed by two holder rods 23. The effect of this feature is to improve the overall stiffness of the arthrodesis apparatus 1 while the joint is being put under compression.

Each of the holder rods 23 then cooperates with an associated oblong cavity 12.

Advantageously, and as shown in the figures, the instrument 20 includes aiming means 30 arranged so as to make it easier to identify the positioning of the fastener means 6 along the nail 5.

In particular, the aiming means 30 are preferably arranged firstly so as to enable the fastener screws 8 to be mounted and guided towards the fastener means 6 provided in the nail 5, and secondly so as to enable the holder rods 23 to be mounted.

In a particularly advantageous manner, the aiming means 30 comprise at least one arm 31 mounted on the base 21 so as to extend substantially parallel to the longitudinal axis X-X'.

The arm 31 is preferably mounted secured to the base 21 so as to remain stationary relative to the base 21 during the compression step and, in particular, while the nail 5 is being moved along the longitudinal axis X-X'.

In a particularly advantageous manner, the aiming means 30 comprise two arms 31 (FIGS. 3-4). The two arms 31 are preferably disposed on either side of the nail 5 in position on the instrument 20, and facing the oblong cavities 12. The two arms 31 are thus preferably disposed laterally relative to the joint so as to enable the fastener screws 8 to be fastened by a lateral approach (FIG. 4).

The use of two arms 31 makes it possible to significantly improve the overall stiffness of the instrument 20 during the compression step, with this configuration serving, in particular, to obtain high compression ratios and to do so without undesirable deflection of the nail 5.

In the preferred exemplary embodiment of the invention shown in FIGS. 3-4, the arms are fastened to the base 21 and extend perpendicularly thereto so as to cooperate with the base 21 to form the compression structure 210. Preferably, the base 21 and the arms 31 are made of metal, and the compression structure 210 forms a one-piece metal unit separate from the connection means 24 and movable relative thereto.

Figure 6:
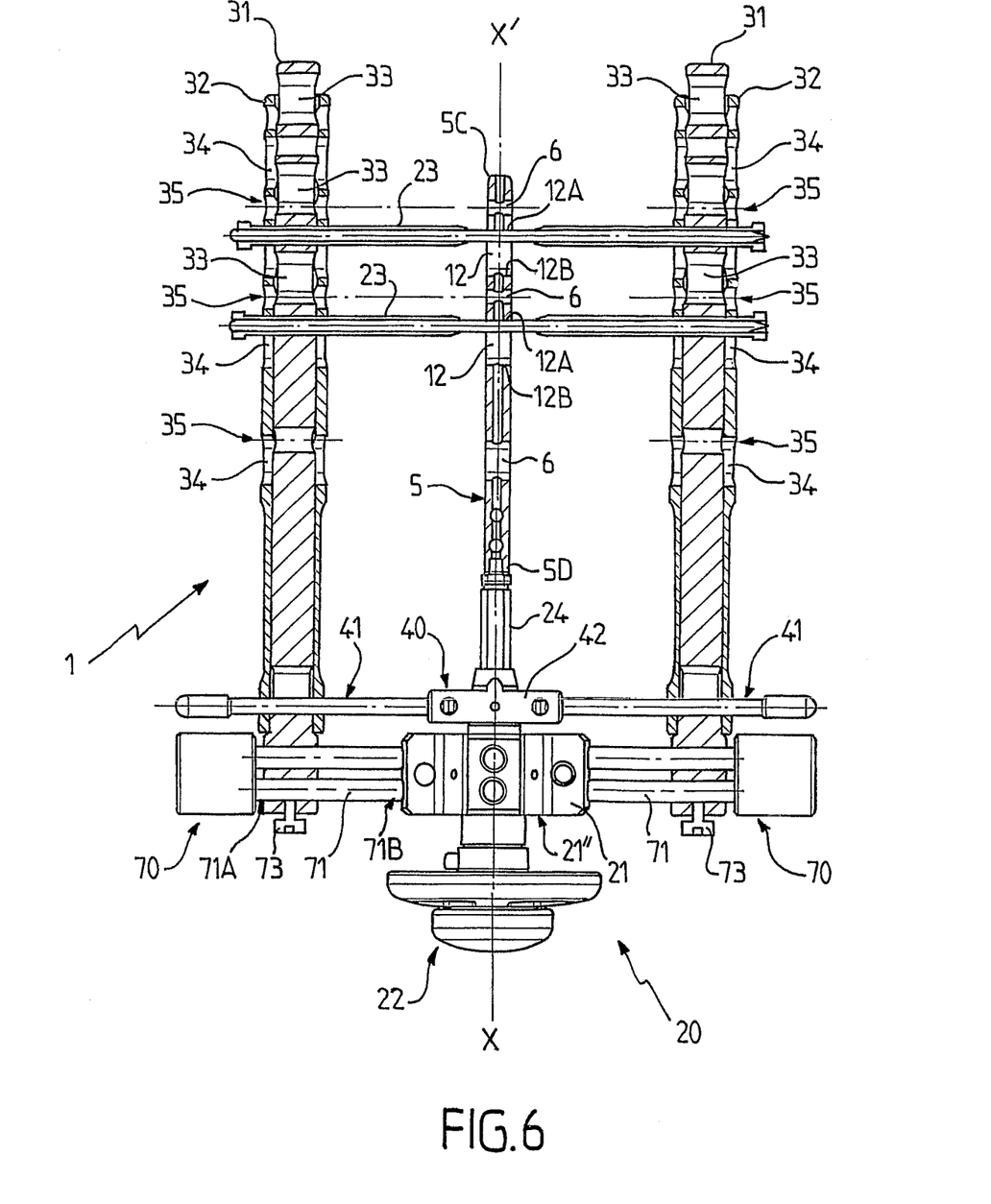
FIG. 6 is a section view showing a variant exemplary embodiment of an arthrodesis apparatus in its position prior to applying compression.

In a variant exemplary embodiment of the present disclosure shown in FIG. 6, the arm 31 is removably mounted on the base 21 via a tab 70. In this exemplary embodiment, the base 21 is in the form of a central core 21". The tab 70 comprises at least one bar 71, preferably in the form of a cylindrical tube extending between two ends 71A, 71B, which tube passes through the arm 31 and is secured thereto towards one of its ends 71A with the help of a clamping button 73.

The other end 71B of the bar 71 is advantageously mounted on the base 21. For this purpose, the base 21 has at least one recess within which one of the ends 71B of the bar 71 can be inserted.

In a still more preferable manner, the tab 70 has two bars 71 and the base 21 has two associated recesses.

Such an assembly can, in particular, be used to adjust the spacing between the arm 31 and the nail 5 by moving the arm 31 along the bars 71 and, in particular, can enable the arm 31 to be moved towards the nail 5 so as to improve the stiffness of the apparatus during the compression step.

Advantageously, the aiming means 30 include at least one sleeve 32 mounted to move on at least one of the arms 31, being free to slide along the longitudinal axis X-X' (FIGS. 3-4). Thus, FIG. 3 shows the arthrodesis apparatus 1 in which the sleeve 32 is in a position prior to applying compression, while FIG. 4 shows the same sleeve 32 in a position after compression has been applied, i.e., after the sleeve 32 has been moved along the longitudinal axis X-X'.

In a particularly advantageous manner, and as shown in FIGS. 3-4, the arm 31 is provided with passages 33 while the sleeve 32 is provided with aiming holes 34. The aiming holes 34 and the passages 33 are arranged in such a manner that by moving the sleeve 32 at least some of the aiming holes 34 can be put into register with some of the passages 33, thereby forming aiming windows 35 each associated in register either with a fastener means 6 or with an oblong cavity 12 (FIG. 4).

Such aiming windows 35 enable a fastener screw 8 or a holder rod 23 to be mounted on the nail 5.

Advantageously, the instrument 20 includes spacer means 40 arranged to secure the sleeve 32 with the link means 24, and thus with the nail 5 in such a manner that movement of the nail 5 along the longitudinal axis X-X' leads to substantially identical movement of the sleeve 32 (FIGS. 3-6).

Advantageously, and as shown in FIGS. 3-4, the spacer means 40 are secured to the link means 24 via the hollow endpiece 84.

The spacer means 40 also include at least one branch 41 secured firstly towards one of its ends to the link means 24, in particular, the hollow endpiece 84, and secondly towards its opposite end, to the sleeve 32, such that movement of the link means 24 leads to substantially identical movement of the sleeve 32. The instrument 20 preferably includes two arms 31 and two associated sleeves 32, and the spacer means 40 preferably comprise two branches 41 associated respectively with each of the sleeves 32.

Preferably, and as shown in FIG. 5, the spacer means 40 and the sleeves 32 form a one-piece unit suitable for moving as a whole.

In a particularly advantageous manner, some of the passages 33 formed through the arm 31 are arranged to support the holder rods and to prevent them from moving relative to the base 21. Amongst the passages 33, those that are associated with the holder rods 23 are preferably substantially cylindrical in shape (FIGS. 3-4).

In addition, the passages 33 and the aiming holes 34 are preferably dimensioned and spaced apart respectively on the arm 31 and on the sleeve 32 in such a manner that, regardless of the movement of the sleeve 32, at least some of the passages 33 remain in register with corresponding aiming holes 34, providing the movement of the sleeve 32 is less than the maximum acceptable stroke corresponding substantially to the length of the oblong cavities 12.

In a preferred exemplary embodiment of the present disclosure, the arthrodesis nail 5 is provided in two preferred embodiments as shown in FIG. 2. Thus, in the particular circumstance of an ankle joint, the nail 5 may be in the form of a first nail 5A presenting a length of about 150 mm, this first nail 5A being more specifically adapted to tibias that are rather short.

In contrast, for tibias that are relatively long, the nail 5 may be in the form of a second nail 5B presenting a length of about 180 mm.

In order to enable the nail 5 to be put into place regardless of its length, the instrument 20, and, in particular, the aiming means 30, are arranged in such a manner as to enable one or the other of the first and second nails 5A, 5B to be mounted. In particular, the arms 31 and the sleeves 32 have respective passages 33 and aiming holes 34 that are specifically adapted for each of the first and second nails 5A, 5B.

In addition, markers can be provided on the sleeves 32, e.g., engraved in the outside surfaces of the sleeve 32, so as to specify which aiming holes 34 should be used with each of the first and second nails 5A, 5B.

Advantageously, and as shown in FIG. 1, the aiming means 30 comprise an aiming support 37 designed to make it easier to identify the positioning of the fastener means 6 of the nail 5 and, in particular, the fastener orifices 9 relative to the first nail 2 (i.e., the calcaneus). The aiming support 37 is intended, in particular, to make it possible, with the help of orifices 140, 141 suitable for receiving jig bushings 143, to enable fastener screws 8 to be put into place that serve to hold the nail 5 relative to the first bone 2.

Preferably, the aiming support 37 is secured to the sleeves 32 via the spacer means 40, thereby forming together with the sleeves 32, an aiming structure 200 that is movable relative to the compression structure 210.

Advantageously, the aiming support 37 is situated in a plane that is substantially perpendicular to the plane interconnecting the sleeve 32 so as to enable the fastener screws 8 to be fastened in the first bone from front to rear.

Preferably, the aiming support 37 and the sleeve 32 and the spacer means 40 are made of plastics material preferably forming an aiming structure 200 of plastics material, advantageously a material that is transparent to X-rays, so as to limit interference with imaging instruments for use during surgery.

Thus, while the nail 5 is being placed within the joint and fastened to the calcaneus, only the aiming structure 200 that is separable from the compression structure 210 is used such that the only metal portion visible to the surgeon is the nail 5.

The aiming structure 200 and the compression structure 210 thus advantageously form one-piece units that are separable one from the other.

In an exemplary embodiment that is not shown, the aiming support 37 may be formed by a part that is independent from the other aiming means 30, being removably mounted on the base 21 via one or more bars.

The arthrodesis apparatus 1 of the present disclosure thus facilitates mounting the arthrodesis nail 5 within the joint while also enabling the bones forming the joint to be moved towards one another in effective and controlled manner.

Because the aiming means 30 are mounted in removable manner, another advantage of the arthrodesis apparatus 1 of the present disclosure is that the arthrodesis nail 5 may be placed in a methodical manner.

Because of the numerous marking means provided, another advantage of the arthrodesis apparatus 1 of the present disclosure is that it is possible to avoid handling errors on the part of the surgeon.

Another advantage of the arthrodesis apparatus 1 of the present disclosure is that it can be taken apart completely thereby making it easier to clean.

The invention also provides an arthrodesis nail having the characteristics described above and suitable for use in the arthrodesis apparatus 1.

More particularly, the present disclosure provides an arthrodesis nail for a joint formed at least by a first bone 2 and by a second bone 3, the nail having fastener means 6 and guide means 11, and being designed for use in an arthrodesis apparatus having holder means 23 in accordance with the present disclosure, the guide means 11 and the holder means 23 are arranged and shaped to cooperate together so as to allow the nail to move relative to the holder means 23, and when the nail 5 is secured to the first bone 3, to allow the first and second bones 2 and 3 to be moved towards each other.

The present disclosure also provides a method of surgery for performing arthrodesis of the ankle joint, in which an arthrodesis apparatus 1 is used, the arthrodesis apparatus 1 comprising an arthrodesis nail 5 and compression means 22, 23, the method comprising the following steps:

securing the nail 5 to the calcaneus; and
a compression step during which firstly the calcaneus is moved closer to the tibia by moving the nail 5 relative to the tibia with the help of the compression means 22, 23, and secondly the amplitude of the displacement of the nail 5 is controlled with the help of the guide means 11 provided on the nail 5.

Advantageously, the compression step is preferably performed using a holder rod 23 that is secured to a stationary portion of the instrument 20 and that is inserted firstly in the tibia so as to prevent the tibia from moving, and secondly in a guide means 11, preferably an oblong cavity 12 formed lengthwise in the nail 5, so that during compression the nail 5 and the associated cavity 12 can move relative to the holder rod 23 over a maximum distance corresponding to the length of the oblong cavity 12.

Thus, because of its oblong shape, the cavity 12 constitutes means for guiding and controlling the movement of the nail 5 and thus the intensity of the compression exerted on the joint. In addition, because of the oblong shape of the cavity 12, the movement of the nail 5 is necessarily movement in translation, thus making it possible to avoid any possible deflection of the nail 5 that might otherwise happen during the compression step.

Furthermore, the positioning of the holder rod 23 in register with the nail 5 during the compression step confers good overall stiffness to the apparatus 1 and makes it possible to perform compression along an axis that is substantially parallel to the axis along which the tibia extends.

The operation of the arthrodesis apparatus 1 and the method of putting the nail 5 into place are described below for the particular circumstance of performing arthrodesis on the ankle.

Before beginning arthrodesis, the surgeon initially takes X-rays enabling the joint to be visualized and enabling the arthrodesis apparatus to be selected, i.e., the nail 5 and the instrument 20 are adapted to the anatomy of the joint.

In particular, for arthrodesis of the ankle, the surgeon may select one or the other of the first and second nails 5A, 5B, as appropriate. In any event, the instrument 20 used is the same and it suffices for the surgeon to select the aiming holes 34 that are suitable for use with the selected nail, with selection being performed with the help of the marker means provided for this purpose on the aiming means 30. Once the appropriate nail has been selected, the surgeon can position the nail on the link means 24 with the help of the marker means 25, 26. Because the nail 5 can be put into only one position on the link means 24, the aiming support 37 and, in particular, the orifices 140 and 141 automatically come into register with the fastener orifices 9 in the nail 5 (FIG. 1).

As is well known to the person skilled in the art, the surgeon must also form a housing for the nail 5 within the joint, this housing passing both through the calcaneus and through a portion of the tibia, and possibly also through the talus.

The housing is preferably made in such a manner that when the nail is inserted into the joint, a pocket 50 situated towards the inside end of the housing formed within the tibia remains unoccupied by the nail 5 (FIGS. 3-4).

When the nail 5 is inserted into the housing, the surgeon proceeds to fasten the nail 5 relative to the calcaneus with the help of the aiming support 37.

The surgeon can then proceed to put the fastener screws 8 into place (FIG. 1) in the fastener orifices 9 using the jig bushings 143 as guides.

Such fastening is well known to the person skilled in the art and does not need to be described in greater detail.

During this first stage of fastening the nail 5 to the calcaneus, the metal compression structure 210 is preferably not used so as to avoid disturbing instruments (for example, amplifier, etc.) with portions made of metal other than the nail 5.

The aiming structure 200 is advantageously made of plastics material so the aiming structure 200 is not "seen" by the instrument, thus enabling the surgeon to visualize the nail 5 more accurately during surgery.

Once the nail 5 is securely fastened to the calcaneus, the surgeon can then proceed with the compression step, i.e., the step that consists of moving the calcaneus closer to the tibia.

The surgeon then mounts the compression structure 210 on the aiming structure 200 by engaging the arms 31 in the corresponding sleeves 32 and by mounting the base 21 on the link means 24 with the possibility of relative sliding.

The compression step is shown in FIGS. 3-4. FIG. 3 shows the arthrodesis apparatus 1 in a position prior to compression in which non-zero clearance J can be seen between the bones 2, 3, and 4 of the joint. In contrast, FIG. 4 shows the arthrodesis apparatus 1 in a position after compression has been applied in which the clearance J is substantially zero.

In order to apply compression, the surgeon must initially insert the tibia holder rods 23 firstly through the passages 33 in the arms 31 and secondly through the oblong cavities 12 in the nail 5. The holder rods 23 thus pass through the tibia 3 so as to prevent the tibia from moving firstly relative to the arms 31 and secondly relative to the base 21.

Once the holder rods 23 have been inserted, the surgeon can actuate the control means 22 and, in particular, the handwheel 80 so as to cause the link means 24 and thus the associated nail 5 to move continuously or stepwise relative to the stationary base 21 (or compression structure 210). The maximum movement allowed for the nail 5 is predetermined by the length of the oblong cavities 12. This maximum allowed movement is preferably about 12 mm.

By preventing the arthrodesis nail 5 from moving farther, it is ensured that the surgeon does not apply excessive compression, which would have the effect of further deteriorating the joint. The particular shape of the oblong cavities 12 thus constitutes first means for controlling the compression ratio exerted on the joint.

As it moves, the nail 5 takes the calcaneus with it, moving the calcaneus progressively towards the tibia while reducing the volume occupied by the pocket 50.

Prior to compression, the holder rods 23 are situated in the top portions of the oblong cavities 12; and after compression has been applied, the holder rods 23 take up position in the central or bottom portions of the cavities 12 (FIG. 4).

It can thus be seen that the ends 12A, 12B of the cavities 12 constitute abutments against which the holder rods 23 come to bear during movement of the nail 5.

The movement of the nail 5 is preferably continuous, but the movement could be discontinuous taking place in steps, particularly with the help of a ratchet system (not shown).

Once the application of compression has terminated, the surgeon can proceed with fastening the nail 5 relative to the tibia, and possibly also relative to the talus. Such a fastening step is shown in FIG. 4.

Once the nail 5 has been secured with all of the bones 2, 3, 4 forming the joint, the aiming structure 200 can be fully separated from the base 21 (or from the compression structure 210) thus making it easier to clean and sterilize the apparatus for future use.

The present disclosure can be used in making arthrodesis nails and apparatus.

All patents, patent applications and publications referred to herein are incorporated by reference in their entirety.

The invention claimed is:

1. An arthrodesis apparatus for a joint, such as an ankle joint, formed by at least a first bone and a second bone, the apparatus comprising:
    a) an arthrodesis nail having a thickness and a longitudinal axis and having
        (i) fastener means adapted to fasten the arthrodesis nail to the bones constituting the joint and
        (ii) guide means formed by at least one cavity provided in the thickness of the arthrodesis nail and extending through the thickness thereof so as to extend along an axis that intersects the longitudinal axis of the arthrodesis nail, the at least one cavity presenting a shape that is substantially elongate along the longitudinal axis;
    b) an instrument for putting the arthrodesis nail into place within the joint, the instrument comprising
        (i) a base that remains stationary with respect to the second bone and
        (ii) compression means comprising control means and holder means, the holder means arranged to prevent the second bone from moving relative to the base, the compression means adapted to enable the first bone forming the joint to be moved towards the second bone, the control means having a force exerting portion adapted to exert a longitudinal force directly on the arthrodesis nail, the force exerting portion being generally coaxial with the base and the arthrodesis nail; and,
    c) link means serving as an interface between the instrument and the arthrodesis nail,
    wherein the control means is arranged so as to act via the link means to move the arthrodesis nail relative to the base along a longitudinal axis substantially parallel to the longitudinal axis along which the arthrodesis nail extends, and
    wherein the guide means and the holder means are arranged and shaped to cooperate together so as to allow the arthrodesis nail to move relative to the holder means and to enable the first bone and the second bone to be moved towards each other once the arthrodesis nail has been secured to the first bone.

2. The apparatus of claim 1, wherein the guide means are formed by at least two elongate cavities formed one above the other along the nail and in alignment with each other along the longitudinal axis.

3. The apparatus of claim 1, wherein the fastener means comprise two fastener holes each designed to cooperate with at least one associated fastener screw so as to secure the nail to the second bone.

4. The apparatus of claim 1, wherein the fastener means of the arthrodesis nail include at least one fastener orifice designed to cooperate with at least one associated fastener screw so as to secure the arthrodesis nail to the first bone.

5. The apparatus of claim 4, wherein the at least one fastener orifice extends obliquely relative to the longitudinal axis.

6. The apparatus of claim 5, wherein the angle formed between the direction in which the at least one oblique fastener orifice extends and the longitudinal axis lies in the range 95° to 100'.

7. The apparatus of claim 5, wherein the fastener means include at least two fastener orifices for fastening the first bone.

8. The apparatus of claim 1, wherein the fastener means include at least one fastener opening arranged to receive an associated fastener screw when the joint includes a third bone situated between the first and second bone, so as to secure the arthrodesis nail substantially with the third bone.

9. The apparatus of claim 8, wherein the fastener opening is oblong.

10. The apparatus of claim 1, wherein the holder means for the second bone is formed by at least one holder rod shaped so as to pass at least in part, both through the second bone so as to hold it stationary relative to the base and through the at least one elongate cavity.

11. The apparatus of claim 10, wherein the holder means is formed by two holder rods.

12. The apparatus of claim 1, wherein the instrument includes aiming means arranged to facilitate identifying the positioning, of the fastener means on the arthrodesis nail.

13. The apparatus of claim 12, wherein the aiming means comprise at least one arm mounted on the base in such a manner as to extend substantially parallel to the longitudinal axis.

14. The apparatus of claim 12, wherein the aiming means comprise an aiming support designed to facilitate identifying the positioning of the fastener means for fastening the arthrodesis nail to the first bone.

15. The apparatus of claim 13, wherein the aiming means comprise two arms disposed on either side of the arthrodesis nail mounted on the instrument, facing the oblong cavities.

16. The apparatus of claim 13, wherein the aiming means include at least one sleeve mounted to move on at least one of the arms adapted to slide along the longitudinal axis.

17. The apparatus of claim 16, wherein the arm is provided with passages while the sleeve is provided with aiming holes, the aiming holes and the passage are arranged in such a manner that by moving the sleeve at least some of the aiming holes will face some of the passages, thus forming aiming windows, each situated in register either with the fastener means or with the at least one elongate cavity so as to enable a fastener screw or a holder rod respectively to be mounted.

18. The apparatus of claim 16, wherein the instrument includes spacer means arranged to secure the sleeve to the arthrodesis nail in such a manner that moving the arthrodesis nail along the longitudinal axis causes substantially identical movement of the sleeve.

19. The apparatus of claim 18, wherein the base and the at least one arm form a compression structure and in that the at least one sleeve and the aiming means form an aiming structure, the aiming structure being mounted to move relative to the compression structure.

20. The apparatus of claim 19, wherein the compression structure is removably mounted relative to the aiming structure.

21. The apparatus of claim 20, wherein the compression structure is made of metal and the aiming structure is made of plastic.

22. The apparatus of claim 1, wherein the link means and the arthrodesis nail include marker means arranged in such a manner as to facilitate positioning the arthrodesis nail relative to the link means.

23. The apparatus of claim 22, wherein the marker means are formed by three studs and by three slots arranged in such a manner that each slot can be associated with only one corresponding stud.

24. The apparatus of claim 1, wherein the control means are formed by a handwheel.

25. A method for performing arthrodesis of an ankle joint incorporating an arthrodesis apparatus comprising an arthrodesis nail and an instrument provided with compression means, the compression means including a threaded rod movable by rotation of a rotatable knob, the method comprising:
a) securing the arthrodesis nail to the calcaneus; and
b) compressing by moving the calcaneus closer to the tibia by moving the arthrodesis nail relative to the tibia with the help of the compression means by rotatably advancing the threaded rod, and controlling the amplitude of the displacement of the arthrodesis nail with the help of guide means provided on the arthrodesis nail.

26. A method for performing arthrodesis of an ankle joint utilizing an arthrodesis apparatus comprising an arthrodesis nail and an instrument provided with compression means, the method comprising:
a) securing the arthrodesis nail to the calcaneus; and
b) compressing by moving the calcaneus closer to the tibia by moving the arthrodesis nail relative to the tibia with the help of the compression means, and controlling the amplitude of the displacement of the arthrodesis nail with the help of guide means provided on the arthrodesis nail, wherein the compressing is performed using a holder rod that is secured to a stationary portion of the instrument, whereby the holder rod is inserted into a portion of the tibia so as to prevent the tibia from moving, and also is inserted in a guide means comprising a cavity formed lengthwise in the arthrodesis nail, the arthrodesis nail being at least partially disposed in the tibia, so that during compression the arthrodesis nail and the associated guide means can move relative to the holder rod over a maximum distance corresponding to the length of the guide means.

27. An arthrodesis apparatus for a joint, such as an ankle joint, formed by at least a first bone and a second bone, the apparatus comprising:
a) an arthrodesis nail having a thickness and a longitudinal axis and having
(i) a plurality of first fastener openings defined in the arthrodesis nail extending transversely to the longitudinal axis each opening sized to receive a first fastener screw adapted to fasten the arthrodesis nail to the bones constituting the joint and
(ii) a plurality of second fastener openings defined in the arthrodesis nail extending transversely to the longitudinal axis and generally parallel to the plurality of first openings, each second fastener opening being elongated along the longitudinal axis of the arthrodesis nail so as to form a slot and sized to receive a second fastener screw;
(iii) at least one third fastener opening extending transversely through the longitudinal axis of the arthrodesis nail at an oblique angle with respect to the longitudinal axis and generally perpendicular to the plurality of first and second fastener holes and sized to receive a third fastener screw,
b) an instrument for inserting and maintaining the arthrodesis nail in place within the joint, the instrument comprising
(i) a base that remains stationary with respect to the second bone, the base including
(A) an elongated generally horizontal first frame member having first and second ends,
(B) a pair of elongated generally vertical second frame members, each having one end associated with one end of the first frame member, each second frame member having a plurality of openings defined therein, each opening able to accommodate either a first fastener screw or a second fastener screw, and
(ii) a compression mechanism comprising a control member having a rod portion and a force generation mechanism for exerting a longitudinal force on the arthrodesis nail, the rod portion and the force generation mechanism being generally coaxial with the base and the arthrodesis nail, the compression mechanism further comprising a holder member arranged to prevent the second bone from moving relative to the base, the compression member adapted to enable the first bone forming the joint to be moved towards the second bone; and
c) a connector link serving as an interface between the instrument and the arthrodesis nail, the connector link being, generally rod-shaped and having a first end adapted to removably abut one end of the arthrodesis nail and a second end adapted to be associated with the control member, the connector link being generally coaxial with the arthrodesis nail when the arthrodesis nail is placed in an abutting relationship therewith, and
d) an aiming member comprising two generally right-angled arms disposed on either side of the horizontal first frame member, and further comprising at least one sleeve mounted to move on at least one of the arms, the sleeve being adapted to slide along the longitudinal axis,
wherein the control mechanism is arranged so as to act via the connector link to move the arthrodesis nail relative to the base along a longitudinal axis substantially parallel to the longitudinal axis along which the arthrodesis nail extends, and wherein the guide member and the holder member are arranged and shaped to cooperate together so to allow the arthrodesis nail to angularly move relative to the holder member and to enable the first bone to be moved towards the second bone once the arthrodesis nail has been secured to the first bone.

* * * * *